United States Patent [19]

Oono et al.

[11] Patent Number: 4,498,005
[45] Date of Patent: Feb. 5, 1985

[54] CASSETTE HAVING RADIATION IMAGE STORAGE MEDIUM

[75] Inventors: Hiroshi Oono; Tsutomu Teshima, both of Kanagawa, Japan

[73] Assignee: Fuji Photo Film Co., Ltd., Kanagawa, Japan

[21] Appl. No.: 440,377

[22] Filed: Nov. 9, 1982

[30] Foreign Application Priority Data

Nov. 14, 1981 [JP] Japan ................................. 56/182703

[51] Int. Cl.³ ............................................ H05B 33/00
[52] U.S. Cl. ................................ 250/327.2; 250/484.1
[58] Field of Search ............... 250/327.2, 483.1, 484.1; 378/167, 182, 187

[56] References Cited

U.S. PATENT DOCUMENTS 3,703,272 11/1972 Lareau ................................. 378/187
4,194,625 3/1980 Stievenart et al. ................. 378/187
4,259,586 3/1981 Schmidt et al. ..................... 378/187

Primary Examiner—Janice A. Howell
Attorney, Agent, or Firm—Sughrue, Mion, Zinn, Macpeak & Seas

[57] ABSTRACT

A cassette for use in a radiation image recording and readout system includes a radiation image storage panel including a layer of stimulable phosphor and having an identification recorded thereon, and a casing for enclosing the radiation image storage panel therein. The casing has an opening provided substantially in correspondence in position with the identification so as to sense it from the outside of the cassette. The identification may be recorded in a visual or magnetically sensable form.

6 Claims, 7 Drawing Figures

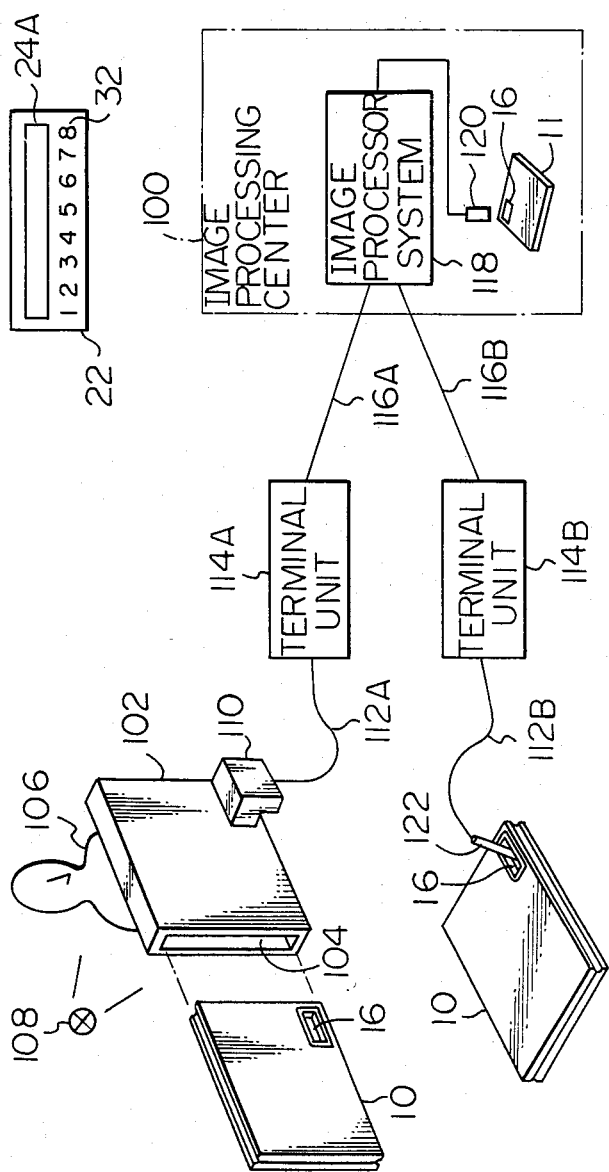

CASSETTE HAVING RADIATION IMAGE STORAGE MEDIUM

BACKGROUND OF THE INVENTION

1. Field of the Invention

The present invention relates to a cassette having a radiation image storage medium, and more specifically but not restricted to a cassette having a radiation image storage panel or plate for use in a radiation image recording and readout system, the storage panel including a sheet of stimulable phosphor, on which a latent image is recorded or stored that is formed by an imagewise radiation impinging thereon.

2. Description of the Prior Art

There have been known some kinds of phosphor which store, when exposed to a radiation, such as an X-ray, α-ray, β-ray, γ-ray or ultraviolet ray, to store a part of the energy of the radiation, and irradiate in association with the stored energy when stimulated afterwards with another radiation such as visible light. Such phosphors may often be referred to as stimulable phosphors.

The assignee of the patent application has proposed a radiation image recording and readout technique utilizing stimulable phosphors, in U.S. Pat. No. 4,258,264 and Japanese Patent Laid-Open Publication No. 11395/1981, for example. In accordance with the proposal, imagewise information carried by radiation transmitted through an object, such as a living body, is first recorded on a sheet of stimulable phosphor, which is then scanned with a stimulative ray generated by a laser, for example, to irradiate rays associated with the recorded information. The emitted rays are sensed by a photoelectric conversion device, that produces a time-serial video signal carrying the imagewise information. The video signal is used to produce a visual image associated with the image information carried therein on a recording medium, such as a sheet of photosensitive material, and/or a cathode-ray tube (CRT) display, for example.

In an application of the above-mentioned technique to medical diagnosis, for example, radiation image storage panels or plates should in practice be maintained in the dark throughout, before and after shooting a radiation image until an image stored therein has been produced as a visual picture, so as not to damage the image stored in the sheet. The stored image would otherwise be damaged by components of natural radiation which have a wavelength ranging from 450 to 1,100 nanometers stimulable to the phoshor as well as ultraviolet rays which may cause radiation energy to be stored as noise in the stimulable phosphor sheet, since such components and rays allow a portion of the stored energy to be dissipated and are stored as noise in the phoshor material. Care should therefore be taken to deal with stimulable phosphor sheets in the dark, and those sheets are in practice enclosed in enclosures or containers, such as a cassette, which contains a single sheet of stimulable phosphor, or a magazine, which contains a plurality of stimulable phosphor sheets.

In hospitals, it is often required to handle a large amount of stimulable phosphor sheets for image processing in a relatively short period of time. Such enclosures having a stimulable phosphor sheet or sheets are transferred from radiation exposure rooms or sites to a radiation image processing center or station. The significant amount of phosphor sheets collected at the center may raise a serious problem of how to identify the respective sheets thus collected.

One of the solutions to the problem is to provide respective stimulable phosphor sheets with specific identifications, such as identification codes or serial numbers, associated with data or particulars related to objects whose images are stored in the phosphor sheets, and enter such information into a computer system in the radiation image processing center. Such data may contain object data specifying an object or patient under radiation exposure, such as name, sex, date of birth and the like, as well as exposure data associated with a radiation exposure, such as data and time of exposure, amount of a radiation irradiated, imaged portion of a body, and the like. When images stored in stimulable phosphor sheets are afterwards read out and produced as visual images, data associated with the sheets are searched for by indexing identifications alotted thereto in the central computer system.

In the case of a cassette, including a single plate of stimulable phosphor, the cassette may be provided with an indication representative of an identification for the phosphor plate contained therein. However, this does not assure a phosphor sheet enclosed in a cassette being associated with the indication provided on the cassette, and it is difficult to know from the outside whether or not a cassette contains a stimulable phosphor sheet.

In the case of a magazine, containing a plurality of stimulable phosphor sheets therein, it is also difficult to determine which sheets are associated with respective indications provided on a magazine and representative of identifications for the respective sheets. If one takes a phospher sheet or sheets out of a cassette or magazine, she will identify the sheet or sheets by means of an identification code indicated thereon, but this is inefficient and increases the possibility of exposing the phosphor sheets to undesired visible, infrared and ultraviolet rays or other radiations, thereby causing noise in an image recorded thereon.

SUMMARY OF THE INVENTION

It is therefore an object of the present invention to provide a cassette having a radiation image storage medium, of which an identification is recognizable from the outside so as to increase the working efficiency of a radiation image record and reproduction system using such cassettes and reduce the possibility of noise which would otherwise be involved in the storage medium.

In accordance with the present invention, a cassette for use in a radiation image recording and readout system comprises a storage medium including a layer of stimulable phosphor for storing therein a latent image formed by an imagewise radiation, said storage medium having an identification recorded thereon, and casing means for enclosing the storage medium therein, said casing means having an opening provided substantially in correspondence in position with the identification so as to permit sensing of the identification from the outside of the cassette.

The identification on the storage medium may be in a visual form.

The storage medium may have a magnetic recording medium on which the identification is magnetically recordable.

The casing means has two main surfaces, through one of which the imagewise radiation impinges onto the layer of stimulable phosphor, the identification being indicated on a portion of the storage panel corresponding to the other of the main surfaces of the casing means, the opening being provided in the other of the main surfaces.

A radiation image storage panel which is advantageously applicable to a cassette in accordance with the present invention may have at least one layer of stimulable phosphor supported on a supporting member. The supporting member may either be colored to be substantially opaque to stimulative rays for the phosphor, or have a layer of light absorbing material provided on a surface of the supporting member opposite to the layer of stimulable phosphor or between the supporting member and the layer of stimulable phosphor. The layer of light absorbing material is substantially opaque to stimulative rays. During manufacturing a supporting member, a coloring agent for absorbing stimulative rays may advantageously be kneaded into a material of which the supporting member is to be made, or a supporting member may be impregnated with a solution containing such a coloring agent from a surface thereof, in order to color the supporting member so as to be substantially opaque to stimulative rays. The aforementioned light absorbing layer may advantageously be provided by applying to a supporting member a coloring agent for absorbing stimulative rays dispersed into an appropriate binder. As a coloring agent for absorbing stimulative rays, one may preferably employ carbon black, and inorganic and organic coloring agents as disclosed in U.S. patent application Ser. Nos. 156,520 and 326,642.

Preferably, a stimulable phosphor applicable to the present invention emits light having a wavelength within the range of 300 to 500 nm in response to stimulating rays having a wavelength within the range of 600 to 700 nm, as disclosed in U.S. Pat. No. 4,258,264. One example of this phosphor is rare earth activated alkaline earth metal fluorohalide phosphor, as described in Japanese Patent Laid-Open Publication No. 12143/1980, a phosphor represented by the formula $(Ba_{1-x-y}, Mg_x, Ca_y)FX:aEu^2$ wherein X is at least one of Cl and Br, x and y are numbers satisfying $0<x+y\leq 0.6$ and $xy\neq 0$, and a is a number satisfying $10^{-6}\leq a \leq 5\times 10^{-2}$. Another example of this phosphor is, as described in U.S. Pat. No. 4,239,968, a phosphor represented by the formula $(Ba_{1-x}, M^{II}_x)FX:yA$ wherein $M^{II}$ is at least one of Mg, Ca, Sr, Zn and Cd, X is at least one of Cl, Br and I, A is at least one of Eu, Tb, Ce, Tm, Dy, Pr, Ho, Nd, Yb and Er, x is a number satisfying $0\leq x\leq 0.6$, and y is a number satisfying $0\leq y\leq 0.2$. Further, as the stimulable phosphor to be used in the present invention can be used ZnS:Cu, Pb; $BaO\cdot xAl_2O_3$:Eu wherein $0.8\leq x\leq 10$: and $M^{II}O\cdot xSiO_2$:A wherein $M^{II}$ is Mg, Ca, Sr, Zn, Cd or Ba, A is Ce, Tb, Eu, Tm, Pb, Tl, Bi or Mn, and x is a number satisfying $0.5\leq x\leq 2.5$, as described U.S. Pat. No. 4,236,078. Furthermore, as the stimulable phosphor can be used LnOX:xA wherein Ln is at least one of La, Y, Gd and Lu, X is at least one of Cl and Br, A is at least one of Ce and Tb, x is a number satisfying $0<x<0.1$, as described in U.S. Pat. No. 4,236,078, also. Among the above numerated phosphors, the rare earth activated alkaline earth metal fluorohalide phosphor is the most preferable, among which barium fluorohalides are the most preferable in view of the high intentisy of emission of light.

For higher intensity of emission of light, use may be made of barium fluorohalides with the addition of metal fluorides as described in Japanese Patent Laid-Open Publication Nos. 2385/1981 and 2386/1981, or those with the addition of at least one of metal chlorides, metal bromides and metal iodides, as disclosed in U.S. patent application Ser. No. 367,665.

Further, it is desirable to color the phosphor layer of the stimulable phosphor plate including the above phosphor by use of pigments or dyes to improve the sharpness of the image obtained thereby, as disclosed in U.S. patent application Ser. No. 156,520.

In the present invention, the stimulable phosphor may be defined as a phosphor which, after exposure to an initial radiation like X-rays, $\alpha$-rays, $\beta$-rays, $\gamma$-rays and ultraviolet rays, emits light of the amount associated with the energy of the stored radiation when stimulated optically.

BRIEF DESCRIPTION OF THE DRAWINGS

The objects and features of the present invention will become more apparent from a consideration of the following detailed description taken in conjunction with the accompanying drawings in which:

FIG. 6 is a partially diagramic, partially schematic diagram showing a radiation image recording and read-out system to which a cassette in accordance with the invention is applicable; and FIG. 7 is a plan view showing another example of a label on which a magnetic recording medium is provided to record thereon an identification code for a radiation image storage panel.

DETAILED DESCRIPTION OF THE PREFERRED EMBODIMENT

Figure 1:
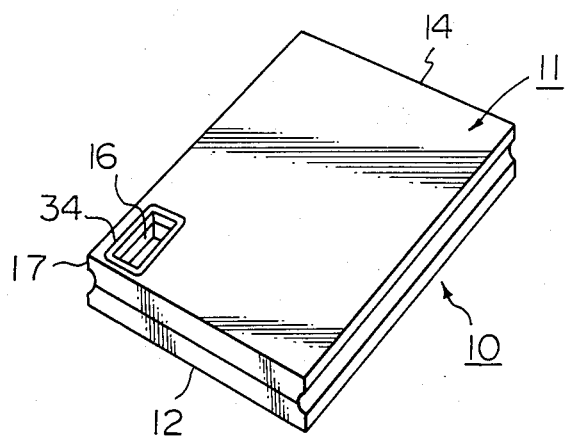
FIG. 1 is a perspective view showing an embodiment of a cassette in accordance with the present invention.
Figure 2:
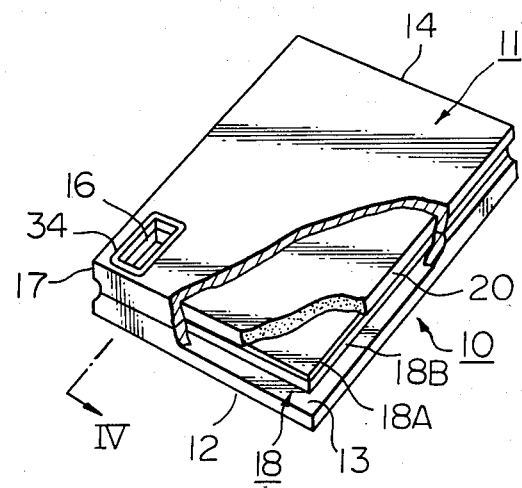
FIG. 2 is a partially cut out, perspective view showing the embodiment depicted in FIG. 1.

With reference to FIGS. 1 and 2, a cassette 10 includes a casing 11 composed of front and back halves 12 and 14. Front half 12 is to be disposed toward a radiation source, such as an X-ray source, and is made of a plastic so as to pass therethrough an imagewise radiation transmitted through an object, such as a living body. Back half 14, which is also made of a plastic, is disposed opposite to front half 12 with respect to a radiation image storage panel or plate 18 contained therein, as shown in FIG. 2. In the illustrative embodiment, back half 14 has a generally rectangular opening 16 in proximity to a corner 17 thereof.

A radiation image storage panel or plate 18 is contained or installed in casing 11 as shown in FIG. 2. In casing 11, also provided is a buffering sheet 20, which is preferably made of spongy rubber or plastic, or foamed synthetic resin, in order to press the entire storage panel 18 uniformly onto the inner surface 13 of front half 12.

Radiation image storage panel 18 may be of $14\times 17$, $10\times 12$, $8\times 10$ and $14\times 14$ inch sizes, and accordingly casing 11 may be of the corresponding sizes so as to enclose those sizes of image storage plate 18.

Figure 3:
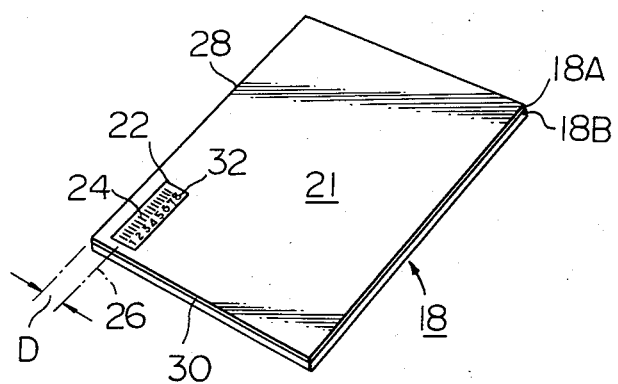
FIG. 3 is a perspective view showing an example of a radiation image storage panel installed in the cassette illustrated in FIG. 1.

As shown in FIG. 3, the radiation image storage panel 18 has a label 22 applied thereto at a predetermined position on a portion of a main surface 21 of panel 18, which surface is opposite to the other main surface upon which an imagewise radiation is to impinge. In the illustrative embodiment, label 22 has a specific identification 24 indicated thereon, which may be a bar code representing a serial number specifying a particular panel 18. Label 22 is positioned in the embodiment in such a manner that the distance D of the center line 26 of bar code 24 from a reference side, e.g. 28, of rectangular plate 18 falls within a predetermined tolerance, with bar code 24 spaced from another side, e.g. 30, perpendicular to the reference side 28 at least by a predetermined spacing. This may facilitate bar code 24 to be sensed by a bar code reader, such as an optical scanner, as discussed later.

In the illustrative embodiment, an identification code represented by bar code 24 may include a binary representation corresponding to eight decimal digits, of which the most significant digit indicates the year of manufacturing storage panel 18, the next six digits indicate a serial number, and the least significant digit represents a check code, such as a parity.

In addition to bar code 24, there is provided a numeral indication 32 of the number represented by the bar code 24, in order for an operator to read numeral indication 32 to identify a specific panel 18.

Figure 4:
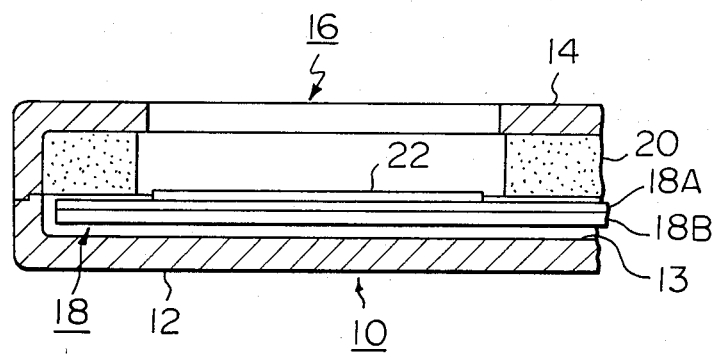
FIG. 4 is a sectional view depicting the section of a portion of the panel taken along the line IV of FIG. 2.

With reference to FIG. 4, in which a cross section of a part of cassette 10 along line IV, FIG. 2, is illustrated, back half 14 of casing 11 has an opening 16 cut therein substantially correspondingly in position and in size to label 22 of image storage panel 18.

In the illustrative embodiment of the invention, a part of radiation image storage panel 18 in cassette 10 may be exposed to external rays impinging through opening 16 of casing 11. However, the image storage panel 18 has a supporting member or a light absorbing layer 18A which supports a layer of stimulable phosphor 18B and is substantially opaque to stimulative rays, as discussed above, so that a latent image stored in image storage panel 18 is not affected by noise due to such external rays.

Experiments were made to prove how external rays impinging through opening 16 affect the stimulable phosphor of image storage panel 18. The results are plotted in FIG. 5, in which illuminance on the surface of image storage panel 18 is depicted on the ordinate with respect to time on the abscissa elapsing from the illumination of external rays to opening 16 of cassette 10. As the light source for the external rays, a general purpose light bulb was employed which satisfies the requirements under the Japanese Industrial Standard, JIS C 7501. Under the experiments, cassettes 10 loaded with image storage panels 18 were exposed to external rays emitted from the light source, and the exposed panels 18 were brought to image reproduction processes to produce visual images on a photosensitive medium, such as a photography film.

Figure 5:
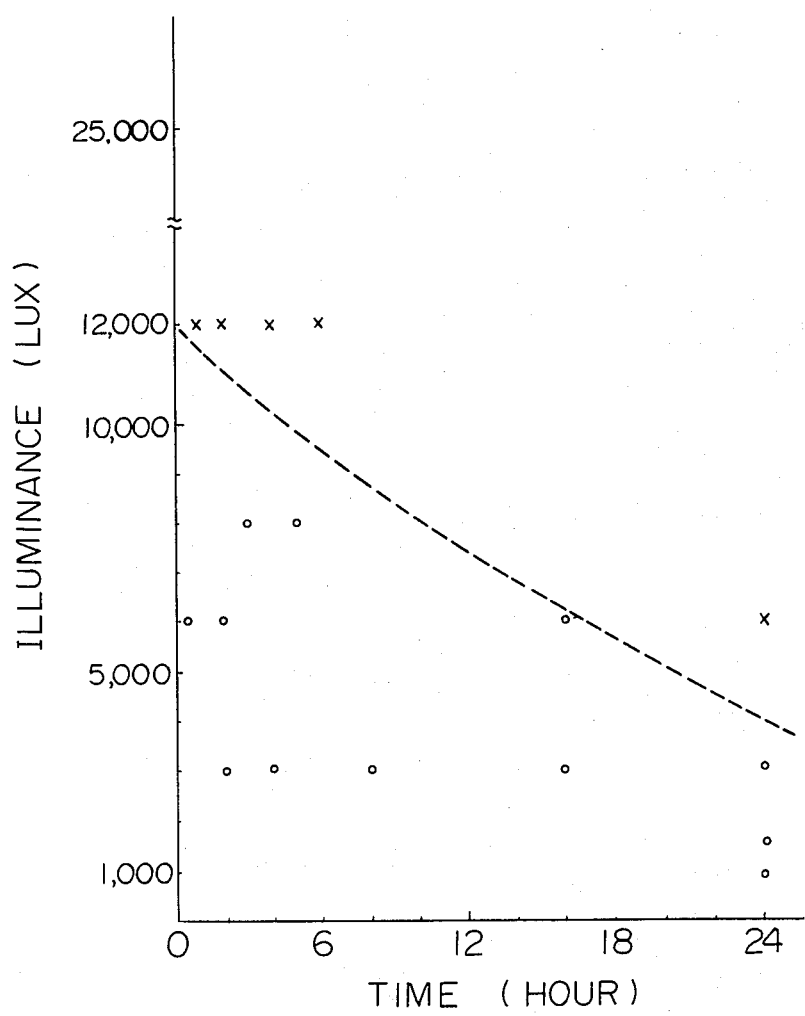
FIG. 5 plots exemplarily an illumination with respect to time effected from the opening provided in a cassette to a radiation image storage panel.

In FIG. 5, the circles plot the data obtained from storage panels 18 which did not have the exposition of the external rays through opening 16 recorded therein, namely, did not produce the images of opening 16 on the photosensitive film, while the marks "x" plot the data from storage panels 18 which had the exposition recorded therein, i.e. produced the images of opening 16 on the film. As can clearly be seen from the chart, under the usual room light environment, cassettes 10 loaded with image storage panel 18 may be left day and night without any effect of external rays on the storage panel 18. Even exposition of external rays of 7,000 through 8,000 lux. does not cause any effect on storage panel 18, if it is done during a short period of time.

In the illustrative embodiment, opening 16 does not have any means for protection. It is however more advantageous to provide opening 16 with a piece of transparent material, such as a sheet of filter glass, which prevents dust from entering the inside of casing 11. In that case, the sheet of filter glass may have the features of absorbing stimulative rays so as not to allow the undesired stimulative rays to pass opening 16, rather than providing image storage panel 18 with a stimulative ray absorption layer or member, such as layer 18A.

Now, with reference to FIG. 6, showing a radiation image recording and readout system in which cassettes in accordance with the invention may advantageously be used. Cassette 10, which is loaded with radiation image storage panel 18 at a radiation image processing center or station 100, is transferred and distributed to a radiation exposure room or site, at which cassette 10 is loaded into a loading portion 104 of a cassette-type exposure unit 102, and is exposed to a radiation, image such as an X-ray, caused by transmitting X-rays through an object, such as a living body 106, from a radiation source 108 so that an image of a portion of the living body 106 is recorded on radiation image storage panel 18 as a latent image thereof.

Exposure unit 102 is provided with an identification sensor device 110, such as a bar code reader, for sensing an identification for image storage plate 18. Sensor device 110 is adapted to sense a bar code 24 recorded on a label 22 of image storage plate 18 by optically scanning label 22 through opening 16. Sensor device 110 has thus a light emitting and scanning section, not shown, which generates a light beam, such as a laser beam, directs the generated beam onto a label 22 through opening 16 and scans the label 22 with the laser beam, and a photosensitive device, not shown, which senses a part of the laser beam reflected on the label 22 to produce electrical signals associated with bar code 24 representing the identification of image storage plate 18. The electrical signals are transmitted on a cable 112A to a terminal unit 11A.

Terminal unit 114A is interconnected by a transmission line 116A to an image processor system 118 in image processing center 100. Terminal unit 114A transmits the electrical signals representative of an identification of storage panel 18 together with those representing object data, including name and date of birth of a patient 106 entered into the system by means of her identification card or clinical chart, as well as exposure data, including date and conditions of exposure, and a portion of a body under exposure entered by means of a keyboard, not shown, by an operator. Image processor system 118, which may be a computer system for image processing, receives those data from terminal units 114A and 114B to store them in a file memory, not shown.

On the other hand, cassette 10 on which a radiation image has been recorded is transferred from a radiation exposure site to image processing center 100, and will be provided for sensing and reproducing the stored image with stimulating rays as a visual picture. Image processor system 118 has a reader 120 connected, which may be similar in function to bar code reader 110 and is adapted to an identification or bar code 24 on label 22 of image storage panel 18.

Image processor system 118 is operable in response to the identification thus sensed to search for the data including object and exposure data stored in the file memory. By indexing the identification of storage plate 18, the data particular to storage plate 18 is picked out among the stored data. In accordance with the particular data thus searched for, control is made by processor system 118 over sensing the latent image stored in plate 18 and visualizing the latent image on a photosensitive film, thereby producing a hard copy of the original radiation image with stability and uniformity in image quality.

As noted in FIG. 6, another terminal unit 114B is provided with a light-pen scanning-type bar code reader 112 connected by a cable 112B. An operator may have a pen scanner 122 run over bar code 24 on label 22 of image storage panel 18 through opening 16 of cassette 10, which is not loaded into exposure unit 102. In response, terminal unit 114B senses an identification code 24 on label 22 with pen scanner 122 to produce and transmit electrical signals representative thereof to the central processor system 118.

In the illustrative embodiment of the invention, radiation image storage panel 18 is provided with a label 22 on which a visible bar code 24 is to be recorded. Alternatively, label 22 may advantageously be provided with a magnetic recording medium 24A, FIG. 7, on which an identification of image storage panel 18 is to be recorded magnetically. In the latter case, terminal units 114A and 114B, as well as central processor system 118 may be provided with magnetic reader apparatus for the magnetic recording medium 24A.

While there has been described and shown above an illustrative embodiment of the invention, it will be appreciated that the invention is not specifically limited thereto. Accordingly, all variations, modifications and equivalent arrangements within the scope of the annexed claims should be considered to be within the scope of the invention.

What is claimed is:

1. A cassette for use in a radiation image recording and readout system comprising:
    a storage medium including a layer of stimulable phosphor for storing therein a latent image formed by an imagewise radiation, a layer of light absorbing material absorbing stimulative rays for said stimulable phosphor layer, and an identification provided on the layer of light absorbing material to be sensable for identifying said storage medium; and
    casing means for enclosing said storage medium therein, said casing means having two main surfaces, one of which transmits the imagewise radiation impinging thereon to the layer of stimulable phosphor, and the other of which opposes the layer of light absorbing material;
    said casing means having an opening provided in said other main surface substantially in correspondence in position with the identification so as to enable sensing of the identification through the opening from the outside of the cassette.

2. A cassette in accordance with claim 1, wherein the identification on the storage medium is in a visual form.

3. A cassette in accordance with claim 1, wherein said storage medium comprises a magnetic recording medium on which the identification is magnetically recordable.

4. A cassette for use in a radiation image recording and readout system comprising:
    a radiation image storage panel including a first layer of stimulable phosphor, and a second layer of light absorbing material absorbing stimulative rays for the stimulable phosphor;
    a recording medium provided on one of the main surfaces of the second layer opposite to the first layer, and having an identification recorded thereon for identifying said storage panel; and
    casing means for enclosing said storage panel therein;
    said casing means having an opening provided substantially in correspondence in position with said recording medium so as to enable sensing of the identification through the opening from the outside of the cassette.

5. A cassette in accordance with claim 4, wherein the identification on the recording medium is a visual form.

6. A cassette in accordance with claim 4, wherein said recording medium comprises a magnetic recording substance on which the identification is magnetically recordable.

* * * * *